US006315986B1

(12) United States Patent
Wong et al.

(10) Patent No.: US 6,315,986 B1
(45) Date of Patent: Nov. 13, 2001

(54) STRIPED DENTIFRICE STABLE TO COLOR BLEEDING

(75) Inventors: Michael Wong, North Brunswick; Michael Prencipe, West Windsor; Jeffrey M. Miller, Sayreville; Claude L. Benz, Belle Mead, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 08/854,504

(22) Filed: May 12, 1997

(51) Int. Cl.[7] .................................................. A61K 7/16
(52) U.S. Cl. .......................... 424/49; 424/400; 424/40 L
(58) Field of Search ............................ 424/49, 400, 40 L

(56) References Cited

U.S. PATENT DOCUMENTS

| 3,929,987 | 12/1975 | Colodney et al. | 424/52 |
|---|---|---|---|
| 4,069,311 | * 1/1978 | Mannara | 424/49 |
| 4,069,312 | 1/1978 | Mannara | 424/49 |
| 4,129,638 | * 12/1978 | Ritze | 264/117 |
| 4,202,878 | * 5/1980 | Ritze | 424/49 |
| 4,459,277 | * 7/1984 | Kosti | 424/7.1 |
| 4,518,578 | * 5/1985 | Hayes et al. | 424/7.1 |
| 4,814,160 | * 3/1989 | Carter et al. | 424/7.1 |
| 5,200,236 | * 4/1993 | Lang et al. | 427/213 |

FOREIGN PATENT DOCUMENTS 9718267   5/1997   (WO) .

* cited by examiner

Primary Examiner—Thurman K. Page
Assistant Examiner—Amy E Pulliam
(74) Attorney, Agent, or Firm—Paul Shapiro

(57) ABSTRACT

A striped dentifrice stable to color bleeding, wherein at least one dentifrice component contains a colorant entrained in a matrix of synthetic wax particles having a melting point range as measured by DSC is between about 40° C. and about 135° C. and the peak endotherm temperature is at least about 65° C., whereby on storage no off-taste is detected in the dentifrice nor is there any observable colorant bleeding into any other dentifrice component.

10 Claims, No Drawings

STRIPED DENTIFRICE STABLE TO COLOR BLEEDING

BACKGROUND OF THE INVENTION

1. Field of the Invention

This invention relates to aesthetically pleasing pleasant tasting multicomponent dentifrices and more particularly to a striped toothpaste or gel wherein there is substantially no colorant bleeding between dentifrice components.

2. The Prior Art

Aesthetic effects have been acknowledged to play an important role in consumer acceptance of many products. In many cases, ornamental effects have been used to distinguish particular products in the marketplace and to identify products having particular distinctive properties. In the dentifrice field, toothpastes and gels which have incorporated therein contrasting colored stripes are known. Such stripes provide an aesthetic effect which the user finds pleasing and promotes the use of the dentifrice, particularly by children.

A major problem impacting the aesthetic appearance of striped toothpaste is the bleeding or migration of color from one component into another. This is especially severe if one colored component is applied to the surface of a white base. For this reason, a colorant that exhibits substantially no visible bleeding is required.

Striped dentifrice products containing water-soluble dyes are known in the prior art as for example, as disclosed in U.S. Pat. Nos. 4,358,437, 4,568,534, and 4,487,757. A disadvantage to the use of water-soluble dyes enumerated in these patents is that visible bleeding is observed.

U.S. Pat. Nos. 3,957,964, 3,929,988, 4,071,614 and 4,348,378 disclose dentifrices containing encapsulated ingredients such as flavors whereby such ingredients are maintained substantially separate from other dentifrice ingredients during manufacture and storage, while subsequently releasing the encapsulated ingredients into the dentifrice during tooth brushing.

It is also known to the art, e.g., U.S. Pat. No. 4,202,878 to encapsulate water insoluble dyes in capsules wherein the shell material is formed from non-toxic naturally occurring waxes such as carnauba wax, candelella wax, castor wax, paraffin wax and bayberry wax. Although encapsulation of the dyes in these natural waxes overcome dye migration and bleeding, waxes such as natural paraffin wax, have been found to have the drawback, that the wax encapsulated dye when incorporated in a dentifrice composition produces an undesirable, waxy-plastic-like taste when stored at room temperature and during accelerated aging conditions, as for example, 6 weeks at 50° C.

Accordingly, there is a need for a colorant composition useful in the striping of aqueous based dentifrices which will essentially eliminate visible colorant bleeding and which does not suffer from the limitations and problems of the prior art.

SUMMARY OF THE INVENTION

By analyzing data on the temperature increase observed by subjecting a wax material to differential scanning calorimetry using a differential scanning calorimeter (DSC), it is possible to observe a state change of the wax under heat application and heat absorption peaks accompanying phase transition and melting of the wax.

In accordance with the present invention, there is provided an aesthetically pleasing, pleasant tasting, substantially non-bleeding, striped dentifrice composition comprised of at least two dentifrice components wherein at least one of the components is a paste or gel containing a colorant entrained in a matrix of a synthetic aliphatic hydrocarbon wax particle wherein no waxy off-taste is imparted to the dentifrice, the wax having a melting point range as determined by DSC between about 40° and about 135° C. and the peak endotherm temperature being at least about 65° C.

DESCRIPTION OF THE PREFERRED EMBODIMENTS

Synthetic aliphatic hydrocarbon waxes useful in the practice of the present invention include as low-molecular weight polyethylene, low-molecular weight polypropylene, synthetic paraffin wax, oxidation products of aliphatic hydrocarbon waxes, such as oxidized polyethylene wax, and block copolymers thereof. A synthetic wax preferred in the practice of the present invention is a synthetic paraffin wax having a melting point in the range between about 38° and about 110° C. and a peak endotherm temperature, as measured by DSC, in the range of about 90° to about 110° C.

Synthetic aliphatic hydrocarbon waxes are predominately derived from the polymerization of hydrocarbon monomers such as ethylene, propylene and the like and have molecular weights below 10,000. Synthetic aliphatic hydrocarbon waxes include polyethylene waxes and Fisher-Tropsch waxes (polymethylene waxes). Synthetic paraffin wax is synthesized by the Fisher-Tropsch process from carbon monoxide and hydrogen, which are catalytically converted to a mixture of paraffin hydrocarbons; the lower molecular weight fractions are removed by distillation, and the residue is hydrogenated and further treated by percolation through activated charcoal. This mixture may be fractionated into its components by a solvent separation method, using a suitable synthetic isoparaffinic petroleum hydrocarbon solvent. Synthetic paraffin waxes are distinguished from paraffin waxes, which are obtained at different stages in the process of refining crude oil. During such process, the different distillates can be separated by different melting points. Refined paraffin wax is the first fraction to come off the refining processing column. Thereafter microcrystalline wax is distilled off.

The synthetic wax entrained colorant particles are incorporated in the dentifrice component at a concentration of about 0.01 to about 5% by weight and preferably about 0.05 to about 1% by weight.

Colorants suitable for entrainment or encapsulation in the synthetic wax matrix in accordance with the practice of the present invention include physiologically compatible water-soluble dyes and lakes including natural or synthetic dyes of the types permitted in foods and drugs, such as those listed in Title 21 of the U.S. Code of Federal Regulations, Section 74, including for example FD&C Blue #1 and FD&C Yellow #10. In addition to these water-soluble dyes, it is also possible to use water-insoluble dyes, for example Eyeshadow Blue KO, Colour Index 77 510, EG-No., Blue 15 (C-Blue 17), or mixtures of water-insoluble dyes and water-soluble dyes, for example Eyeshadow Blue KO and Lemon Yellow ZN 3, in which case green hues are obtained. Preferred colorants are comprised of 1% to 40% by weight, preferably 10% to 30% by weight, of a water soluble dye on a substrate such as alumina, zirconia and titania and preferably alumina hydrate. Preferred lakes are those certified by the Color Certification Laboratory of the Food and Drug Administration of the Health, Education and Welfare Department of the United States Government, for example, F.D. & C. Blue No. 1 Lake, F.D. & C. Blue No. 2 Lake, F.D. & C. Red No. 3 Lake, F.D. & C. Yellow No. 5 Lake and F.D. & C. Yellow No. 6 Lake.

The colorant may be entrained in the synthetic wax using methods of encapsulation which are known in the art. As these encapsulation methods are not specific parts of the present invention, they will not be described at length herein. Further disclosure of suitable encapsulation methods may be found in Kirk-Othmer Encyclopedia of Chemical Technology, Third Edition, Vol. 125 Pgs. 470–493 (1981) which publication is hereby incorporated by reference.

An example of a method by which colorants such as lakes of the present invention may be entrained in a synthetic wax matrix, such as synthetic paraffin wax, is by mixing about 30–70% by weight of synthetic paraffin wax particles with about 25–35% by weight of an appropriate oil dispersant material to which is added the desired amount of colorant material. The desired amount of colorant material is that amount of colorant which results in a final concentration of up to 20% colorant, preferably 1–10% by weight colorant in the final dried colored synthetic wax particles. A second method of entrainment is by dispersing or dissolving the dye or lake in a synthetic wax that has been thermally softened to form a liquid composition. The dispersion is agitated so that the liquid wax deposits on each entity of the dye or lake material forming liquid wax walled droplets. The dispersion is then cooled to provide solid particles in which the dye or lake is entrained.

In the preparation of a dentifrice composition in accordance with the present invention, there is utilized an orally acceptable vehicle, including a water-phase with humectant which is preferably glycerine or sorbitol or an alkylene glycol such as polyethylene glycol or propylene glycol, wherein the water is present typically in amount of about 5 to about 20% by weight and the glycerine, sorbitol and/or the alkylene glycol humectant ingredients typically total about 20–60% by weight of the dentifrice, more typically about 25 to 50%.

Abrasive compounds may be present in the dentifrice and include silica, insoluble sodium metaphosphate, potassium metaphosphate, tricalcium phosphate, dihydrated dicalcium phosphate, calcium carbonate, aluminum silicate, hydrated alumina, sodium bicarbonate, and calcined alumina. Preferred abrasives include silica, and dicalcium phosphate. Silica abrasives useful in the practice of the present invention are available under the trade designation Zeodent 115. The abrasive is generally present in the dentifrice composition of the present invention in weight concentrations of about 15 to about 60% by weight.

Suitable thickeners or gelling agents used to prepare the dentifrice of the present invention include thickening silicas sold under the trade designation Zeodent 165, natural or synthetic organic materials including Irish moss, iota-carrageenan, gum tragacanth, starch, polyvinylpyrrolidone, hydroxyethylpropyl cellulose, hydroxybutyl methyl cellulose, hydroxypropyl methyl cellulose, hydroxyethyl cellulose and sodium carboxymethyl cellulose. The thickener or gelling agent is present in the dentifrice composition in proportions of about 0.1 to about 10% by weight, preferably about 2 to about 8% by weight.

Surfactants are used in the compositions of the present invention to achieve increased prophylactic action and render the dentifrice compositions more cosmetically acceptable. The surfactant is preferably a detersive material which imparts to the composition detersive and foaming properties. Suitable examples of surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, sodium lauryl sulfoacetate and higher fatty acid esters of 1,2-dihydroxy propane sulfonate. The surfactant is typically present in the dentifrice compositions of the present invention in an amount of about 0.3 to about 5% by weight, preferably about 0.5 to about 2% by weight.

Anticaries agents which provide a source of fluoride ions may be included in the dentifrice composition in amount sufficient to supply about 25 ppm to 5,000 ppm of fluoride ions, such as soluble alkali metal salts, for example, sodium fluoride, potassium fluoride, and sodium monofluorophosphate.

In addition to fluoride compounds, there may also be included in the dentifrice composition antitartar agents such as pyrophosphate salts including dialkali or tetraalkali metal pyrophosphate salts such as $Na_4P_2O_7$, $Ka_4P_2O_7$, $Na_4K_2P_2O_7$, $Na_4H_2P_2O_7$ and $K_2H_2P_2O_7$ long chain polyphosphates such as sodium hexametaphosphate, sodium tripolyphosphate and cyclic phosphates such as sodium trimetaphosphate which are included in the dentifrice composition at a concentration of about 1 to about 5% by weight.

Synthetic anionic polymeric polycarboxylates may also be used in the dentifrice compositions of the present invention. Such anionic polymer polycarboxylates are generally employed in the form of their free acids or preferably partially or more preferably fully neutralized water soluble alkali metal, e.g., potassium and preferably sodium or ammonium salts. Preferred polycarboxylate compounds are 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000 most preferably about 30,000 to about 500,000. These copolymers are commercially available, for example, as Gantrez, e.g. AN 139 (M.W. 500,000), AN 119 (M.W. 250,000); and preferably S-97 Pharmaceutical Grade (M.W. 70,000).

The dentifrice composition of the present invention may also contain a flavoring agent. The flavoring agent is incorporated in the dentifrice composition at a concentration of about 0.1 to about 5% by weight and preferably about 0.5% about 1.5% by weight. Flavoring agents which are used in the practice of the present invention include essential oils as well as various flavoring aldehydes, esters, alcohols, and similar materials. Examples of the essential oils include oils of spearmint, peppermint, wintergreen, sassafras clove, sage, eucalyptus, marjoram, cinnamon, lemon, lime, grapefruit, and orange. Also useful are such chemicals as menthol, carvone, and anethole. Of these, the most commonly employed are the oils of peppermint and spearmint.

Various other materials may be incorporated in the dentifrice compositions of this invention, including antibacterial agents such as Triclosan, chlorhexidine, desensitizers such as potassium nitrate, whitening agents such as hydrogen peroxide, calcium peroxide and urea peroxide, preservatives, silicones, and chlorophyll compounds. These adjuvants, when present, are incorporated in the dentifrice composition in amounts which do not substantially adversely affect the properties and characteristics desired.

The preparation of dentifrices compositions is well known in the art. U.S. Pat. Nos. 3,996,863, 3,980,767, 4,328,205 and 4,358,437, which are incorporated herein by reference, describe toothpastes and methods of production thereof which may be utilized for production of the dentifrices according to the present invention.

Dentifrice striping can be accomplished by either of the two techniques common in the art, namely surface striping and deep striping. Surface striping is created by a special nozzle through which the dentifrice is extruded from a tube or pump dispenser, wherein a separate reservoir of stripe material is positioned so that the initial deposition of the stripe on the base dentifrice segment is during extrusion. In deep striping systems by contrast, the layers of striping and base material are juxtapositioned in the dispenser in the pattern of the desired stripes, hence the initial deposition of the stripe on the base dentifrice is prior to extrusion from the dispenser. With surface striping, the quantity of striping material to base material in surface striping is generally in the ratio of about 5:95 to about 20:80; whereas, in deep striping the range can extend from about 10:90 to about 50:50. U.S. Patents which further exemplify such striping methods include U.S. Pat. Nos. 3,969,767, 3,135,428, 2,914,220, 2,905,364, 2,873,887 and 2,789,731.

The following examples are illustrative of the subject invention, and do not limit it. All parts or percentages are by weight and all temperatures are in degrees C, unless specifically stated to be otherwise.

EXAMPLE I

Two dentifrice formulations were formulated with different ingredients one containing baking soda and calcium peroxide (Dentifrice A) and the second containing the antibacterial agent Triclosan (Dentifrice B). The ingredients of these dentifrices are listed in Table I below.

TABLE I

| Ingredient | Dentifrice A | Dentifrice B |
| --- | --- | --- |
| Glycerin 99.7% | 26.00 | 20.00 |
| Carrageenan | 0.20 | — |
| Carboxymethyl cellulose | 0.20 | — |
| Sodium saccharin | 0.50 | 0.30 |
| Sodium monofluorophosphate | 0.76 | — |
| Propylene glycol | 14.89 | — |
| Sodium hydroxide | 1.50 | 1.20 |
| Tetrasodium pyrophosphate | 2.00 | — |
| Sodium tripolyphosphate | 3.00 | — |
| Water, deionized | 9.50 | 18.06 |
| Zeodent 115 | 21.00 | 20.00 |
| Zeodent 165 | 1.50 | 1.30 |
| Sodium bicarbonate | 16.00 | — |
| Sodium carboxymethyl cellulose | — | 0.80 |
| Iota carrageenan | — | 0.30 |
| Sodium fluoride | — | 0.24 |
| Sorbitol (70%) | — | 19.50 |
| Gantrez liquid | — | 15.00 |
| Triclosan | — | 0.30 |
| Flavor | 0.95 | 1.00 |
| Sodium lauryl sulfate | 1.50 | 1.50 |
| Wax capsules with entrained lake* | 0.5 | 0.5 |
| TOTAL | 100.00 | 100.00 |

*Lake is F.D. & C. Blue No. 1 Lake (alumina). Wax capsules were comprised of synthetic paraffin wax containing 2% by weight lake.

The waxes in which the dyes were entrained and their melting point ranges (by DSC) are listed in Table II. Table II also records whether or not an undesirable waxy-, plastic-like taste was detected when Dentifrice Compositions A and B were stored (aged) 2 to 6 weeks at room temperature (25° C.) and under accelerated aging conditions(50° C.).

TABLE II

| Wax Encapsulant | Melting Points As Determined by DSC | | Aging Condition | Waxy-Taste Detected? | |
| --- | --- | --- | --- | --- | --- |
| | Range (° C.) | Peak Endotherm (° C.) | | Dentifrice A | Dentifrice B |
| Refined Paraffin | 25–70 | 66 | 2 weeks at 25C. | Yes | — |
| | | | 2 weeks at 50C. | Yes | — |
| | | | 5 days at 25C. | — | Yes |
| | | | 2 weeks at 50C. | — | Yes |
| Microcrystalline | 35–95 | 66–77 | 6 weeks at 25C. | No | No |
| | | | 6 weeks at 50C. | No | No |
| Synthetic Paraffin A* | 40–110 | 98 | 6 weeks at 25C. | No | No |
| Synthetic Paraffin B** | 38–99 | 70–85 | 4 weeks at 25C. | No | No |
| | | | 4 weeks at 50C. | No | No |

*Synthetic paraffin wax available from International Group, Inc. Agin Court, Ontario, Canada and identified as Fisher Tropsch wax, CAS Registry Number 8002-74-2 having a boiling point (IPBX) of 343° C. and a freezing point (ASTM D87) of 70° C.
**Synthetic paraffin wax available from Koster Keunen, Inc., Watertown, CT. having a molecular weight of 750, CAS Registry Number 8002-4-2.

The results recorded in Table II indicate that a waxy taste was detected in Dentifrices A and B when the wax encapsulant was a refined paraffin wax, whereas no waxy taste was detected when the encapsulant was a microcrystalline wax or a synthetic paraffin wax.

EXAMPLE II

A striped dentifrice was obtained by combining the blue Dentifrice Composition A of Example I with a white pigmented paste having substantially the same composition as Dentifrice A except that 1% by TiO2 was used instead of the wax entrained blue lake and the water content of the dentifrice was adjusted to accommodate the composition change.

Toothpaste tubes were filled with the blue and white colored dentifrices using the deep striping filling system previously described whereby the striped portions were of equal volume. The tubes containing the striped dentifrice were aged at 50° C. for varying time periods. To determine the level of any bleeding that may have occurred during aging, a striped sample of at least 4 inches in length was dispensed from the tubes onto a paper sheet. With the end of a capillary tube (90 mm diameter—closed end), a 0.1 gram toothpaste sample was taken about 0.1–0.2 inches from the blue-white stripe interface. The paste sample was dissolved in 1 milliliter (ml) water and stirred in a Vortex to ensure a complete mixture of the sample so that the dye in the paste was resolubilized in the water phase. The sample was then centrifuged for 2–3 minutes to separate the supernatant (containing the dissolved dye) from the other dentifrice ingredients. Using an ultraviolet visible spectrophotometer, the extinction coefficient at the wavelength at which maximum absorbance of light occurs (lambda max) that is, 630 nm for FD&C Blue 1 was determined before and after aging. The amount of dye that migrated from the blue striped gel to the white paste was determined from Beers Law:

$$A = \epsilon l c$$

where

A=absorbance at $\lambda$max $\epsilon$=extinction coefficient for dye ($cm^{-1} M^{-1}$)

l=length of sample cell (usually 1 cm)

c=concentration (M)

The percent dye bleeding was calculated by dividing absorbance of the FD&C Blue-1 dye detected in the white paste component versus a control wherein the procedure of Example II was repeated with the exception that the blue lake was not entrained in any material. The results are recorded in Table III below.

For purposes of comparison, the above identified procedure was repeated except the blue lake was entrained in the microcrystalline wax in which no waxy taste had been detected in the aging tests performed in Example I. The bleeding results for this comparative wax are also recorded in Table III below.

TABLE III

| Wax Encapsulant | Aging Conditions | | Absorbance @ 630 nm | | % Bleeding Detected in White Paste |
|---|---|---|---|---|---|
| | Weeks | Temperature | Gel Side | Paste Side | |
| Synthetic Paraffin Wax A | 6 | 25° C. | 0.072 | 0.00354 | 5 |
| | 6 | 50° C. | 0.072 | 0.00387 | 5 |
| Synthetic Paraffin Wax B | 3 | 25° C. | 0.087 | 0.00678 | 8 |
| | 3 | 50° C. | 0.087 | 0.00621 | 7 |
| Microcrystalline Wax | 6 | 25° C. | 0.076 | 0.0187 | 25 |
| | 6 | 50° C. | 0.076 | 0.0231 | 30 |
| Control | 6 | 25° C. | 0.078 | 0.0549 | 70 |
| | 6 | 50° C. | 0.078 | 0.0662 | 85 |

The results recorded in Table III indicate that entrainment of the blue lake in the synthetic paraffin waxes significantly reduced dye bleeding when compared to a microcrystalline wax and the control. The percent bleeding of 5–8% that occurred when the blue lake was encapsulated in synthetic paraffin waxes A and B was unperceivable to the naked eye whereas the bleeding of 24–30% that occurred when the blue lake was encapsulated in the microcrystalline wax was clearly visible to the naked eye.

We claim:

1. A striped dentifrice composition stable to color bleeding comprising a plurality of components, at least one component having a colorant entrained in a matrix of synthetic wax particles, the wax having a melting point range as determined by differential scanning calorimetry of between about 40° and about 135° C. and a peak endotherm temperature of at least about 65° C., whereby after storage, substantially no detectable off-taste is detected in the dentifrice and substantially no colorant is observable as migrating into any other dentifrice component.

2. The composition of claim 1 wherein the synthetic wax is a synthetic paraffin wax.

3. The dentifrice composition of claim 1 wherein the melting point range of the wax is between 38 and 99° C. and the peak endotherm temperature is about 70° C. to about 85° C.

4. The dentifrice composition of claim 1 wherein the melting point range of the wax is between about 40 and about 110° C. and the peak endotherm temperature is about 98° C.

5. The dentifrice composition of claim 1, wherein the colorant is a physiologically compatible lake.

6. A method of preparing a non-bleeding striped dentifrice comprising preparing a plurality of dentifrice components and providing in at least one component a colorant entrained in a matrix of synthetic wax particles having a melting point range as determined by differential scanning calorimetry is between about 40° C. and about 135° C. and a peak endotherm temperature of at least about 70° C.

7. The method of claim 6 wherein the synthetic wax is a synthetic paraffin wax.

8. The method of claim 6 wherein the melting point range of the wax is between about 38° and about 99° C. and the peak endotherm temperature is about 70° C. to about 85° C.

9. The method of claim 6 wherein the melting point range is between 40° and about 110° C. and the peak endotherm temperature is about 98° C.

10. The method of claim 6, wherein the colorant is a physiologically compatible lake.

* * * * *